US012023124B2

(12) United States Patent
Maughan et al.

(10) Patent No.: US 12,023,124 B2
(45) Date of Patent: Jul. 2, 2024

(54) DETECTION OF DISENGAGEMENT IN CABLE DRIVEN TOOL

(71) Applicant: Verb Surgical Inc., Santa Clara, CA (US)

(72) Inventors: Spencer Maughan, Santa Clara, CA (US); Alireza Hariri, Santa Clara, CA (US)

(73) Assignee: Verb Surgical Inc., Santa Clara, CA (US)

( * ) Notice: Subject to any disclaimer, the term of this patent is extended or adjusted under 35 U.S.C. 154(b) by 996 days.

(21) Appl. No.: 16/990,620

(22) Filed: Aug. 11, 2020

(65) Prior Publication Data

US 2022/0047347 A1 Feb. 17, 2022

(51) Int. Cl.
*A61B 34/00* (2016.01)
*G01L 5/04* (2006.01)
(Continued)

(52) U.S. Cl.
CPC .............. *A61B 34/71* (2016.02); *G01L 5/047* (2013.01); *G05B 19/4155* (2013.01);
(Continued)

(58) Field of Classification Search
CPC .................... A61B 34/71; A61B 17/29; A61B 2017/00123; A61B 2017/2932;
(Continued)

(56) References Cited

U.S. PATENT DOCUMENTS

| 6,786,896 | B1 * | 9/2004 | Madhani | ............... | A61B 34/30 606/1 |
| 8,343,141 | B2 * | 1/2013 | Madhani | ............... | A61B 34/71 606/1 |

(Continued)

FOREIGN PATENT DOCUMENTS

| CA | 2633137 C | * 10/2012 | ............. A61B 34/30 |
| CA | 3100291 A1 | * 11/2019 | ............. A61B 34/20 |

(Continued)

OTHER PUBLICATIONS

Gaussian Process Regression for Sensorless Grip Force Estimation of Cable Driven Elongated Surgical Instrument (Year: 2017).*

(Continued)

*Primary Examiner* — Jonathan L Sample
*Assistant Examiner* — Shaheda Shabnam Hoque
(74) *Attorney, Agent, or Firm* — Lempia Summerfield Katz LLC

(57) ABSTRACT

The disclosed embodiments relate to systems and methods for a surgical tool or a surgical robotic system. One example system for detecting disengagement of a surgical tool, includes an end effector connected to and driven by cables of a tool driver, sensors configured to detect forces associated with the cables, and one or more processors. The one or more processors identify cable tensions derived from forces detected by the sensors, compare the tension to a threshold tension value, calculate a velocity norm value based on a vector including the velocity value for each of the cables, compare the velocity norm value to a statistic velocity (Continued)

Figure 1:
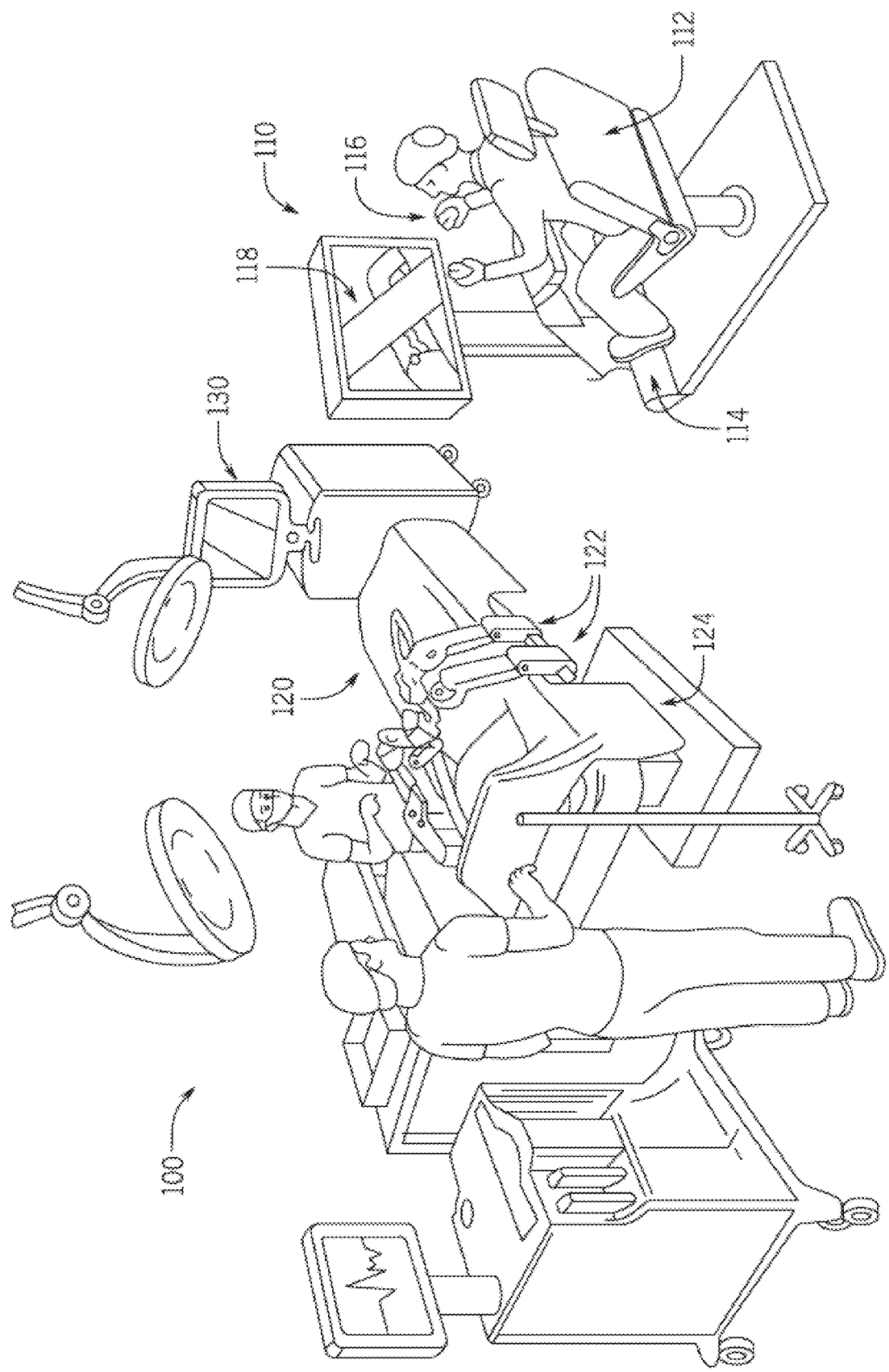
Figure 2:
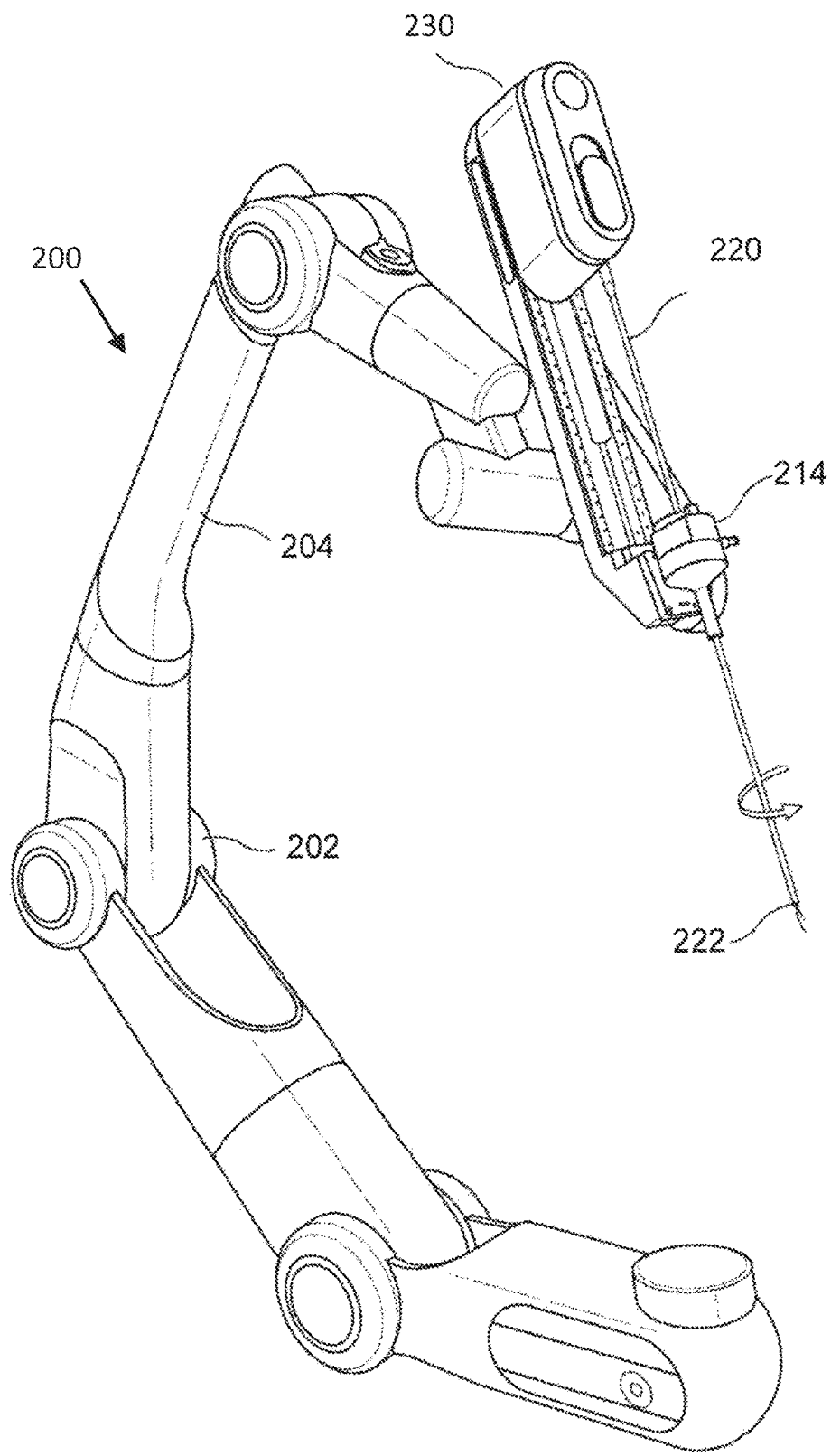

threshold, and identify a disengagement of at least one of the plurality of cables based on the first comparison and the second comparison.

20 Claims, 11 Drawing Sheets

(51) Int. Cl.
| | |
|---|---|
| *G05B 19/4155* | (2006.01) |
| *A61B 17/00* | (2006.01) |
| *A61B 17/29* | (2006.01) |
| *A61B 34/30* | (2016.01) |
| *A61B 90/00* | (2016.01) |

(52) U.S. Cl.
CPC ..... *A61B 2017/00123* (2013.01); *A61B 17/29* (2013.01); *A61B 2017/2932* (2013.01); *A61B 2034/302* (2016.02); *A61B 2090/064* (2016.02); *A61B 2090/066* (2016.02); *G05B 2219/45123* (2013.01)

(58) Field of Classification Search
CPC ........ A61B 2034/302; A61B 2090/064; A61B 2090/066; A61B 34/30; A61B 2090/0808; A61B 2090/0809; A61B 90/06; A61B 2017/00119; G01L 5/047; G01L 5/0042; G05B 19/4155; G05B 2219/45123; G16H 40/63; G16H 40/40
See application file for complete search history.

(56) References Cited

U.S. PATENT DOCUMENTS

| | | | |
|---|---|---|---|
| 10,143,360 B2* | 12/2018 | Roelle | A61B 34/30 |
| 10,448,813 B2* | 10/2019 | Cooper | A61B 1/00154 |
| 2013/0197307 A1* | 8/2013 | Ashida | A61B 1/00148 |
| | | | 600/114 |
| 2014/0357953 A1* | 12/2014 | Roelle | A61B 1/0016 |
| | | | 600/118 |
| 2015/0209965 A1* | 7/2015 | Low | B25J 17/02 |
| | | | 901/29 |
| 2016/0066773 A1* | 3/2016 | Cooper | A61B 1/00149 |
| | | | 600/104 |
| 2016/0287840 A1 | 10/2016 | Jiang | |
| 2018/0311831 A1 | 11/2018 | Guerin | |
| 2019/0274769 A1* | 9/2019 | Perdue | A61B 34/35 |
| 2020/0054401 A1 | 2/2020 | Yu et al. | |
| 2020/0146765 A1* | 5/2020 | Hibner | A61B 17/00234 |

FOREIGN PATENT DOCUMENTS

| | | |
|---|---|---|
| JP | 2013248119 A | 12/2013 |
| WO | 2018148030 A1 | 8/2018 |

OTHER PUBLICATIONS

International Search Report and the Written Opinion for International Patent Application PCT/IB2021/057405 dated Nov. 19, 2021.
U.S. Appl. No. 16/818,938, filed Mar. 13, 2020 by Edgar Ignacio Ergueta Tejerina and Alireza Hariri, "Detecting Cable Breakage on Cable Driven Tools".

* cited by examiner

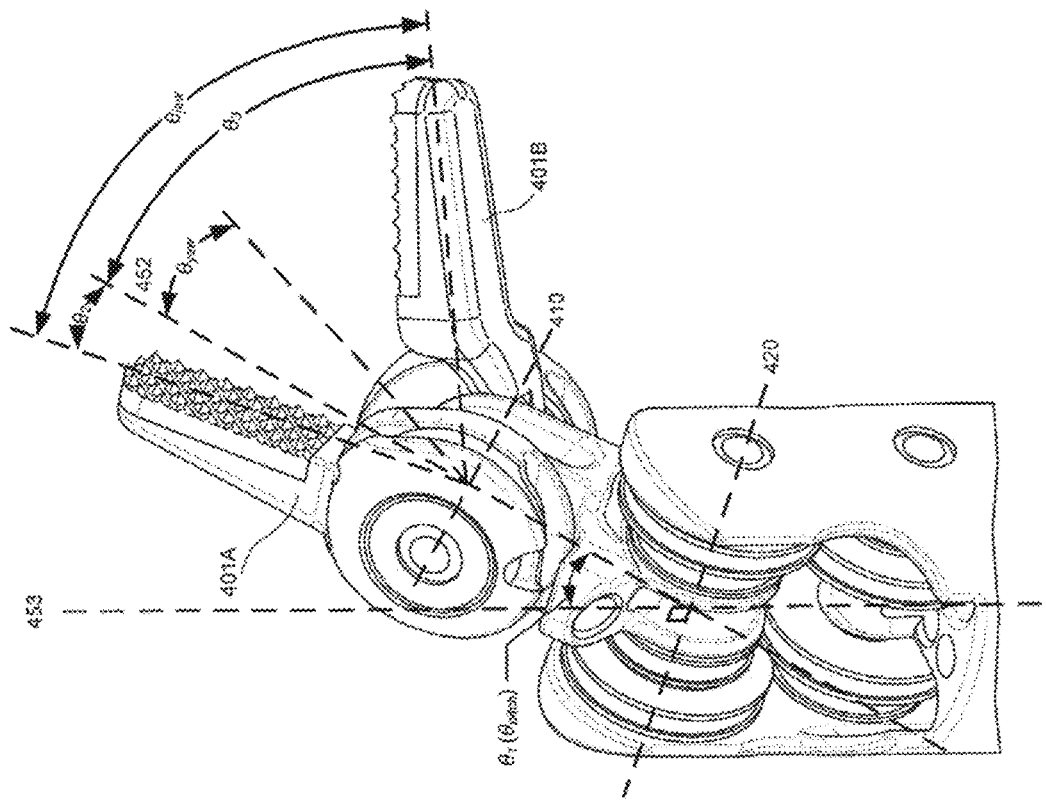
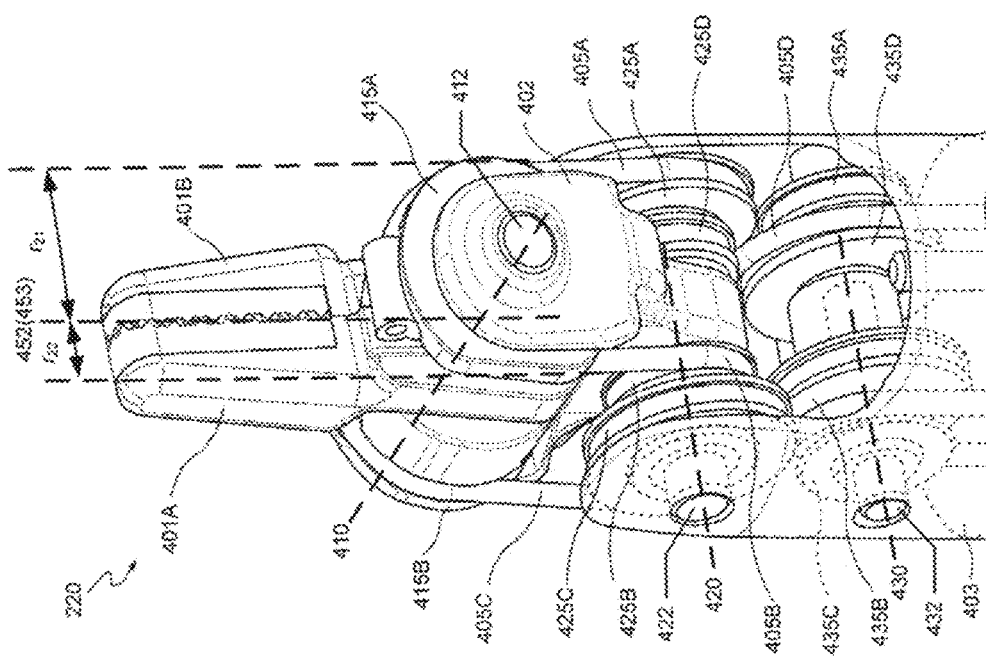
FIG. 4B
FIG. 4A

DETECTION OF DISENGAGEMENT IN CABLE DRIVEN TOOL

FIELD

This disclosure relates to the detection of a disengagement, breakage, or other failure in a cable for driving a surgical tool.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more surgical tools (e.g., end effectors or endoscope) through the incisions into the patient. The surgical procedures may then be performed using the introduced surgical tools, with the visualization aid provided by the endoscope.

Generally, MIS provides multiple benefits, such as reduced patient scarring, less patient pain, shorter patient recovery periods, and lower medical treatment costs associated with patient recovery. Recent technology development allows more MIS to be performed with robotic systems that include one or more robotic arms for manipulating surgical tools based on commands from a remote operator. A robotic arm may, for example, support at its distal end various devices such as surgical end effectors, imaging devices, cannulae for providing access to the patient's body cavity and organs, etc. In but in other configurations, the robotic arms may be mounted in a cart, a ceiling, a sidewall, or other suitable support surfaces.

Generally, a user, such as a surgeon or other operator, may be seated at the user console 110 to remotely manipulate the robotic arms 122 and/or surgical instruments (e.g., teleoperation). The user console 110 may be located in the same operation room as the robotic system 100, as shown in FIG. 1. In other environments, the user console 110 may be located in an adjacent or nearby room, or teleoperated from a remote location in a different building, city, or country. The user console 110 may comprise a seat 112, pedals 114, one or more handheld user interface devices (UIDs) 116, and an open display 118 configured to display, for example, a view of the surgical site inside a patient. As shown in the exemplary user console 110, a surgeon sitting in the seat 112 and viewing the open display 118 may manipulate the pedals 114 and/or handheld user interface devices 116 to remotely control robotic arms 122 and/or surgical instruments mounted to the distal ends of the arms 122.

In some variations, a user may also operate the surgical robotic system 100 in an "over the bed" (OTB) mode, in which the user is at the patient's side and simultaneously manipulating a robotically-driven tool/end effector attached thereto (e.g., with a handheld user interface device 116 held in one hand) and a manual laparoscopic tool. For example, the user's left hand may be manipulating a handheld user interface device 116 to control a robotic surgical component, while the user's right hand may be manipulating a manual to the graspers (e.g. open/close, yaw, and pitch). A set of bipolar forceps includes two tips designed to grasp, manipulate and coagulate selected tissue and also operate in a similar manner to the graspers (e.g. open/close, yaw, and pitch).

As shown in FIG. 4A, the pair of opposing jaws 401A and 401B are movably coupled to a first yoke 402 of the robotic wrist via an extended axle 412 along a first axis 410. The first yoke 402 may be movably coupled to a second yoke 403 of the robotic wrist via a second extended axle 422 along a second axis 420. The pair of jaws 401A and 401B may each be coupled or integrally formed with pulleys 415A and 415B respectively, via the extended axle 412, so that both jaws can rotate about the axis 410. Pulleys 425A, 425B, 425C and 425D are coupled to the extended axle 422 and rotate around the axis 420. The pulleys 425A, 425B, 425C and 425D are arranged into a first set of pulleys 425B and 425C on one side of the yoke 402 and a second set of pulleys 425A and 425D on the other side of the yoke 402. The pulleys 425A and 425C are outer pulleys and the pulleys 425B and 425D are inner pulleys. Similarly, the third set of pulleys 435A, 435B, 435C and 435D are coupled to a third extended axle 432 and rotate around the axis 430, which is parallel to the axis 420.

The end effector 222 (grasper) can be actuated to move one or both of the jaws 401A and 401B in a variety of ways around the axis 410. For example, the jaws 401A and 401B may open and close relative to each other. The jaws 401A and 401B may also be actuated to rotate together as a pair to provide a yaw motion of the end effector 222 (grasper). In addition, the first yoke 402, the pulleys 415A and 415B, and the jaws 401A and 401B can rotate about the axis 420 to provide a pitch motion of the end effector 222

The angular position and grip force of a distal end effector of a robotic surgical instrument is described. The end effector may include a robotic wrist and a pair of opposing members (e.g., jaws or claws), each being movable between an open position and a closed position actuated by two antagonistic cables. A total of four cables may each be driven by an independent actuator or motor. The control system may include feedback loops involving position and velocity feedback from the actuators and force feedback measured on the four cables, to effect desired position and grip force. In some implementations, the actuator controllers may be running a position plus feedforward current mode. For example, a position controller may drive the distal end effector to the desired angular position in space based on the positional feedback, while a grip force controller provides additional feedforward current based on the grip force measured by load cells on the four cables to achieve the desired grip force between the opposing members.

Figure 5:
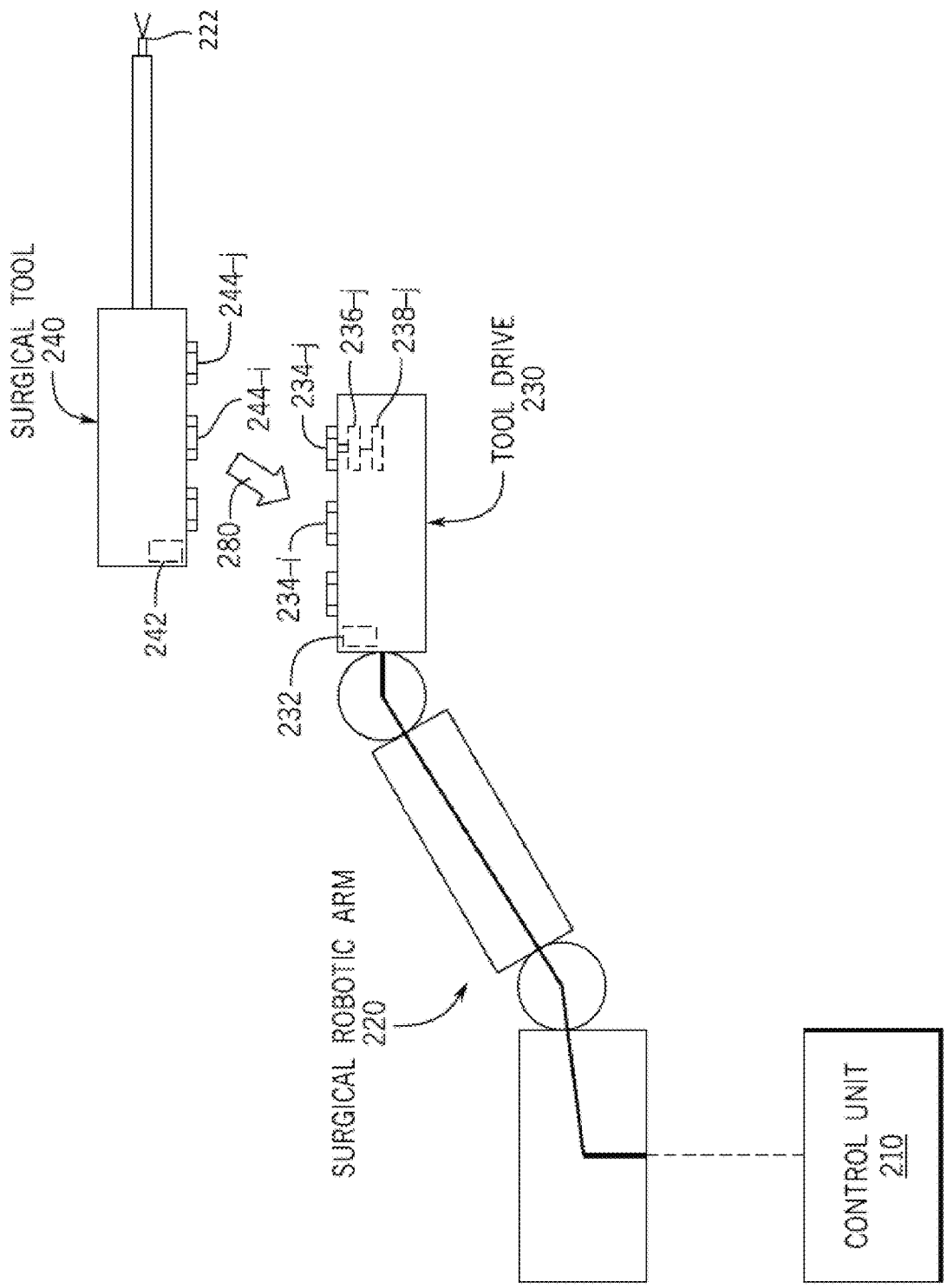

FIG. 5 is an illustration of a subsystem or a part of the surgical robotic system 100, for detecting engagement of a surgical tool 240 to a tool driver 230 (tool driver) of a surgical robotic arm 122. The surgical robotic arm 122 may be one of the surgical robotic arms of surgical robotic system 100 illustrated and discussed with respect to FIG. 1. The control unit 210 may be part of for example the control tower in FIG. 1. As discussed in more detail herein, the engagement may be detected by control unit 210 based on one or more rotary motor operating parameters of one or more actuators (e.g., actuator 238-j) in the tool driver 230. respond to one or more user commands received via a local or remote user input (e.g., joystick, touch control, wearable device, or other user input device communicating via console computer system.) Alternatively, the control unit 210 may respond to one or more autonomous commands or controls (e.g., received form a trained surgical machine learning model that is being executed by the control unit 210 or by the console computer system), or a combination thereof. The commands dictate the movement of robotic arm 122 and operation of its attached end effector 222.

An end effector 222 may be any surgical instruments, such as jaws (e.g., as shown in FIGS. 4A and 4B), a cutting tool, an endoscope, spreader, implant tool, etc. Different surgical tools each having different end effectors can be selectively attached (one at a time) to robotic arm 122 for use during a surgical or other medical procedure. The end effector 222 may be jaws located at a distal end of the surgical tool 240 and that may be retracted into, or extend out of, a cannula as shown (e.g., a thin tube that may be inserted into a patient undergoing a surgical procedure).

The robotic arm 122 includes a tool driver 230, in which there are one or more actuators, such as actuator 238-$j$. Each actuator may be a linear or rotary actuator that has one or more respective electric motors (e.g., a brushless permanent magnet motor) whose drive shaft may be coupled to a respective drive disk 234-$j$ through a transmission (e.g., a gear train that achieves a given gear reduction ratio). The tool driver 230 includes one or more drive disks 234 that may be arranged on a planar or flat surface of the tool driver 230, wherein the figure shows several such drive disks that are arranged on the same plane of the flat surface. Each drive disk (e.g., drive disk 234-$j$) is exposed on the outside surface of the tool driver 230 and is designed to mechanically engage (e.g., to securely fasten via snap, friction, or other mating features) a mating tool disk 244-$j$ of the surgical tool 240, to enable direct torque transfer between the two. This may take place once for example a planar or flat surface of the surgical tool 240 and corresponding or mating planar or flat surface of the tool driver 230 are brought in contact with one another.

Furthermore, a motor driver circuit (for example, installed in the tool driver 230 or elsewhere in the surgical robotic arm 122) is electrically coupled to the input drive terminals of a constituent motor of one or more of the actuators 238. The motor driver circuit manipulates the electrical power drawn by the motor in order to regulate for example the speed of the motor or its torque, in accordance with a motor driver circuit input, which can be set or controlled by control unit 210, which results in the powered rotation of the associated drive disk (e.g., drive disk 234-$j$).

When the mating drive disk 234-$j$ is mechanically engaged to a respective tool disk 244-$j$, the powered rotation of the drive disk 234-$j$ causes the tool disk 244-$j$ to rotate, e.g., the two disks may rotate as one, thereby imparting motion on, for example, linkages, gears, cables, chains, or other transmission devices within the surgical tool 240 for controlling the movement and operation of the end effector 222 which may be mechanically coupled to the transmission device.

Different surgical tools may have different numbers of tool disks based on the types of movements and the number of degrees of freedom in which the movements are performed by their end effectors, such as rotation, articulation, opening, closing, extension, retraction, applying pressure, etc.

Furthermore, within the surgical tool 240, more than one tool disk 244 may contribute to a single motion of the end effector 222 to achieve goals such as load sharing by two or more motors that are driving the mating drive disks 234, respectively. In another aspect, within the tool driver 230, there may be two or more motors whose drive shafts are coupled (via a transmission) to rotate the same output shaft (or drive disk 234), to share a load.

In yet another aspect, within the surgical tool 240, there may be a transmission which translates torque from two drive disks 234 (via respective tool disks 244) for performing complimentary actions in the same degree of freedom, e.g., a first drive disk 234-$j$ rotates a drum within the housing of the surgical instrument 240 to take in one end of a rod, and a second drive disk 234-$i$ rotates another drum within the housing of the surgical instrument 240 to take in the other end of the rod. As another example, the extension and the shortening of an end effector along a single axis may be achieved using two tool disks 234-$i$, 234-$j$, one to perform the extension and another to perform the retraction. This is in contrast to an effector that also moves in one degree of freedom (e.g., extension and shortening longitudinally along a single axis of movement) but that only needs a single tool disk to control its full range of movement. As another example, an effector that moves in multiple degrees of freedom (e.g., such as a wristed movement, movement along multiple axes, activation of an energy emitter in addition to end effector movement, etc.) may necessitate the use of several tool disks (each being engaged to a respective drive disk). In another type of surgical tool 240, a single tool disk 244 is sufficient to perform both extension and retraction motions, via direct input (e.g., gears). As another example, in the case of the end effector 222 being jaws, two or more tool disks 244 may cooperatively control the motion of the jaws, for load sharing, as discussed in greater detail herein.

In yet another aspect, within the surgical tool 240, there may be a transmission which translates torque from two drive disks 234 (via respective tool disks 244) for performing complimentary actions in the same degree of freedom, e.g., a first drive disk 234-$i$ rotates a drum within the housing of the surgical tool 240 to take in one end of a cable, and a second drive disk 234-$j$ rotates another drum within the housing of the surgical tool 240 to take in the other end of the cable. As another example, the extension and the shortening of an end effector along a single axis may be achieved using two tool disks 234-$i$, 234-$j$, one to perform the extension and another to perform the retraction, for example via different cables. This is in contrast to an effector that also moves in one degree of freedom (e.g., extension and shortening longitudinally along a single axis of movement) but that only needs a single tool disk to control its full range of movement. As another example, an effector that moves in multiple degrees of freedom (e.g., such as a wristed movement, movement along multiple axes, activation of an energy emitter in addition to end effector movement, etc.) may necessitate the use of several tool disks (each being engaged to a respective drive disk). In another type of surgical tool 240, a single tool disk 244 is sufficient to perform both extension and retraction motions, via direct input (e.g., gears). As another example, in the case of the end effector 246 being jaws, two or more tool disks 244 may cooperatively control the motion of the jaws, for load sharing, as discussed in greater detail herein.

Figure 6:
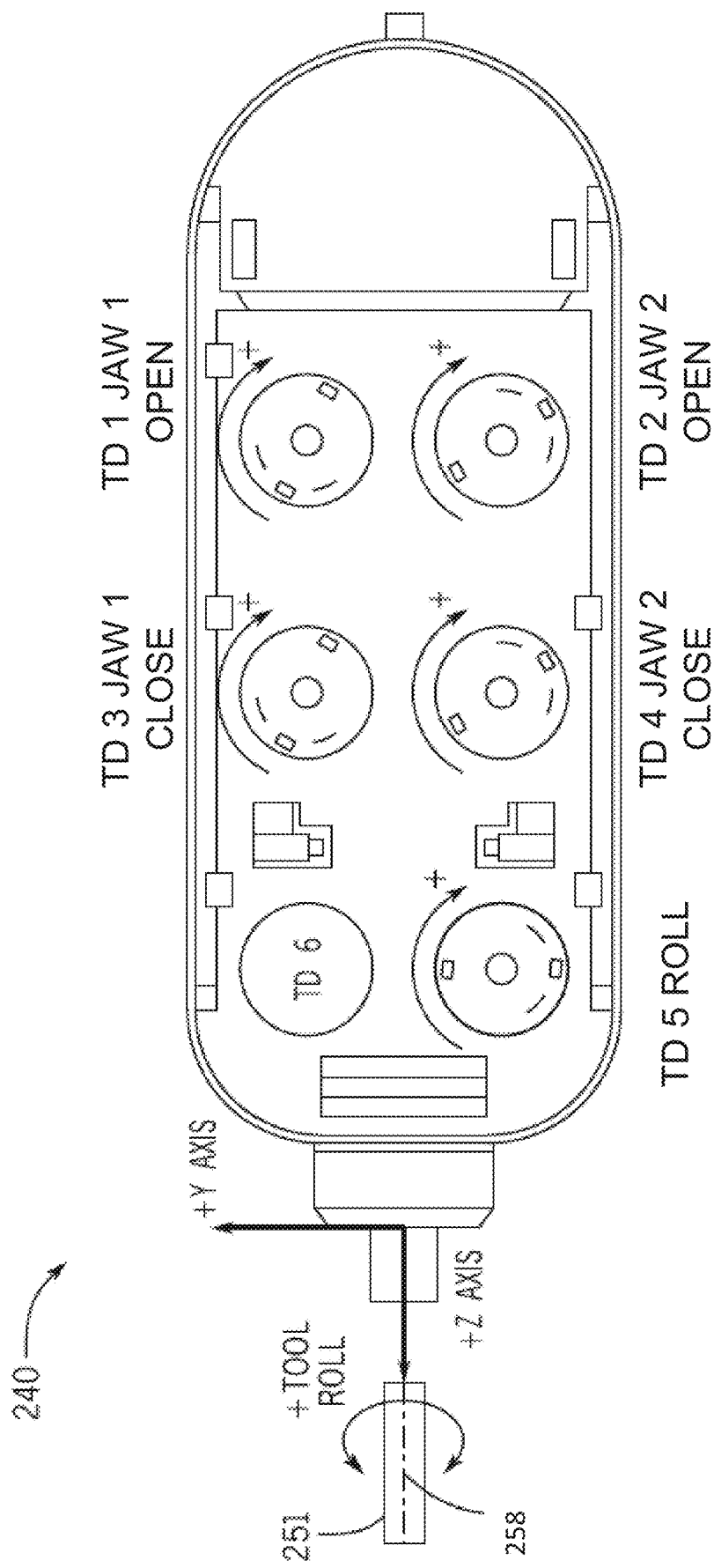

FIG. 6 illustrates an example of the surgical tool 240 including rotary device assignments or mapping for tool disks TD1-5 (TD6 is unused in this example). In this example, tool disk TD5 is mapped to the roll axis 258 of the end effector, which is illustrated as jaw 251 and may comprise a first opposing jaw 401A and a second opposing jaw 401B. The tool disk TD5 may be coupled to one or more gears that drive the wrist to rotate about the roll axis. Each opposing jaw is assigned two tool disks. For example, the first opposing jaw 401A may be assigned to tool disk TD1 for opening the jaw (i.e., increasing the angle between the first opposing jaw 401A and the second opposing jaw 401B) and tool disk TD3 for closing the jaw (i.e., decreasing the angle between the first opposing jaw 401A and the second opposing jaw 401B). The tool disk TD1 may be coupled to a cable that rotates pulley 415A in a first direction and the tool disk TD3 may be coupled to a cable for rotating pulley 415A in a second direction.

Similarly, the second opposing jaw 401B may be assigned to tool disk TD2 for opening the jaw (i.e., increasing the angle between the first opposing jaw 401A and the second opposing jaw 401B) and tool disk TD4 for closing the jaw (i.e., decreasing the angle between the first opposing jaw 401A and the second opposing jaw 401B). The tool disk TD2 may be coupled to a cable that rotates pulley 415B in a first direction and the tool disk TD4 may be coupled to a cable for rotating pulley 415B in a second direction.

In some embodiments, when surgical tool 240 is first attached to or installed on tool driver 230 such that the tool disks are brought substantially into coplanar and coaxial alignment with corresponding drive disks (though the tool and drive disks are perhaps not yet successfully engaged), control unit 210 initially detects the type of the surgical tool 240. In one embodiment, surgical tool 240 has an information storage unit 242, such as a solid state memory, radio frequency identification (RFID) tag, bar code (including two-dimensional or matrix barcodes), etc., that identifies its tool or end effector information, such as one or more of identification of tool or end effector type, unique tool or end effector ID, number of tool disks used, location of those tool disks being used (e.g., from a total of six possible tool disks 244-e, f, g, h, i, j), type of transmission for the tool disks (e.g., direct drive, cable driven, etc.), what motion or actuation a tool disk imparts on the end effector, one or more tool calibration values (e.g., a rotational position of the tool disk as determined during factor testing/assembly of the tool), whether motion of the end effector is constrained by a maximum or minimum movement, as well as other tool attributes. In one embodiment, the information storage unit 242 identifies minimal information, such as a tool ID, which control unit 210 may use to perform a lookup of the various tool attributes.

The tool driver 230 may include a communication interface 232 (e.g., a memory writer, a near field communications, near field communication (NFC), transceiver, RFID scanner, barcode reader, etc.) to read the information from the information storage unit 242 and pass the information to control unit 210. Furthermore, in some embodiments, there may be more than one information storage unit in surgical tool 240, such as one information storage unit associated with each tool disk 244. In this embodiment, tool driver 230 may also include a corresponding sensor for each possible information storage unit that would be present in a given tool.

After surgical tool 240 is attached with tool driver 230, such that tool disks are brought into alignment and are superimposed on corresponding drive disks (although not necessarily mechanically engaged), and after the tool disk information is obtained, e.g., read by control unit 210, the control unit 210 performs an engagement process to detect when all of the tool disks that are expected to be attached to respective drive disks are mechanically engaged with their respective drive disks (e.g., their mechanical engagement has been achieved, or the tool driver 230 is now deemed engaged with the tool). That is, attaching the surgical tool 240 with the tool driver 230 does not necessarily ensure the proper mating needed for mechanical engagement of tool disks with corresponding drive disks (e.g., due to misalignment of mating features). The engagement process may include activating one or more motors of an actuator (e.g., actuator 238-j) that drives a corresponding drive disk 234-j. Then, based on one or more monitored motor operating parameters of the actuator 238-j, while the latter is driving the drive disk 234-j, the mechanical engagement of the tool disk 244-i with a drive disk 234-j can be detected. This process may be repeated for every drive disk 234 (of the tool driver 230) that is expected to be currently attached to a respective tool disk 244 (e.g., as determined based on the tool disk information obtained for the particular surgical tool 240 that is currently attached.)

Upon detecting that a particular type of surgical tool 240 has been attached with the tool driver 230, the control unit 210 activates one or more actuators (e.g., motors) of the tool driver 230 that have been previously associated with that type of surgical tool 240. In some embodiments, each actuator that is associated with a corresponding drive disk 234 of surgical tool 240 may be activated simultaneously, serially, or a combination of simultaneous and serial activation.

Figure 7:
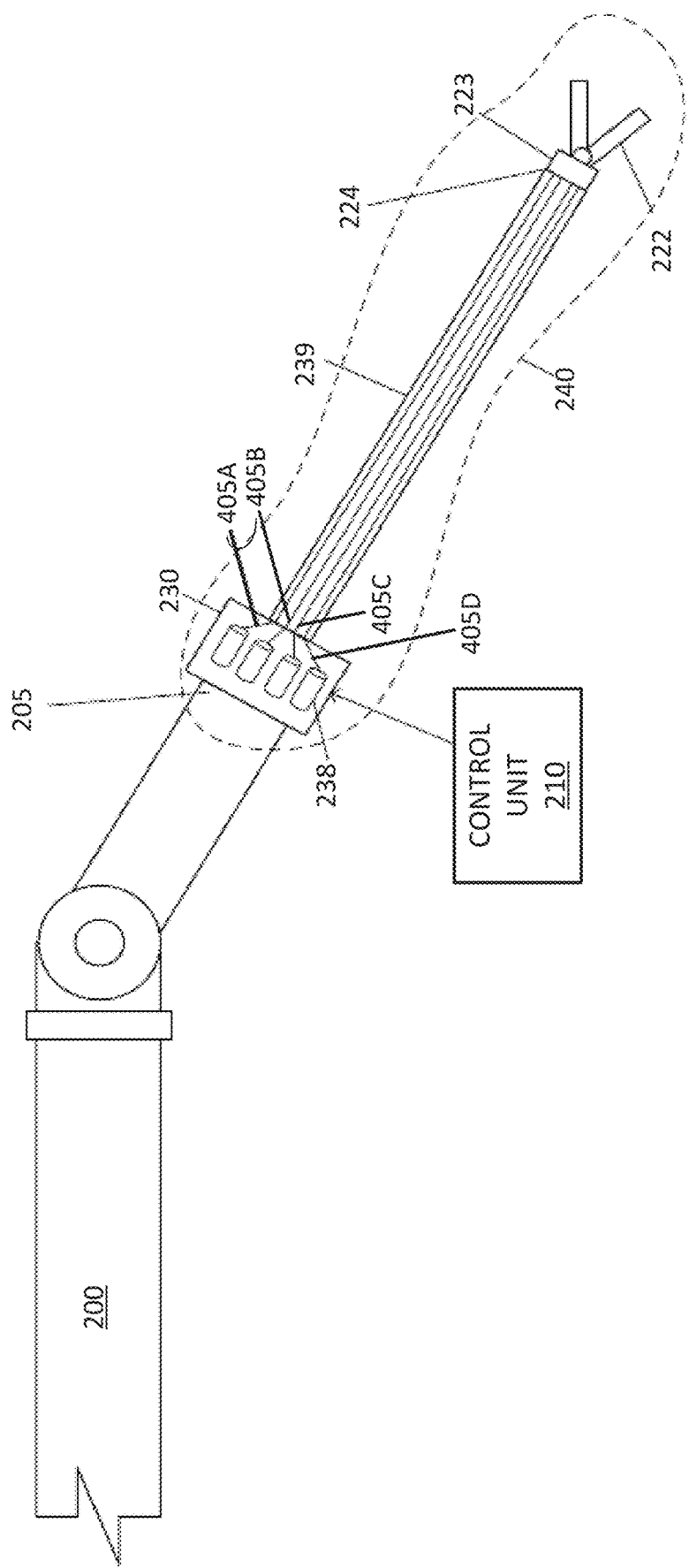

FIG. 7 illustrates the cable drive system for the surgical tool 240. As described in other embodiments herein, four cables 405A-D are driven by the tool driver 230 to provide a desired position or motion to a tool, which includes a wrist 223 and the end effector 222. The cables 405A-D connect to the wrist 223 at a cable interface 224. The wrist 223 is connected to the end effector 222, or includes the end effector 222. The cables 405A-D are contained and protected by a shaft 239. The cables connect to the distal end of the robotic arm 200 at a tool attachment interface 205. A control unit 210 provides data to one or more components of the surgical tool 240 and receives feedback data from the surgical tool 240, as described in more detail below.

Figure 8:
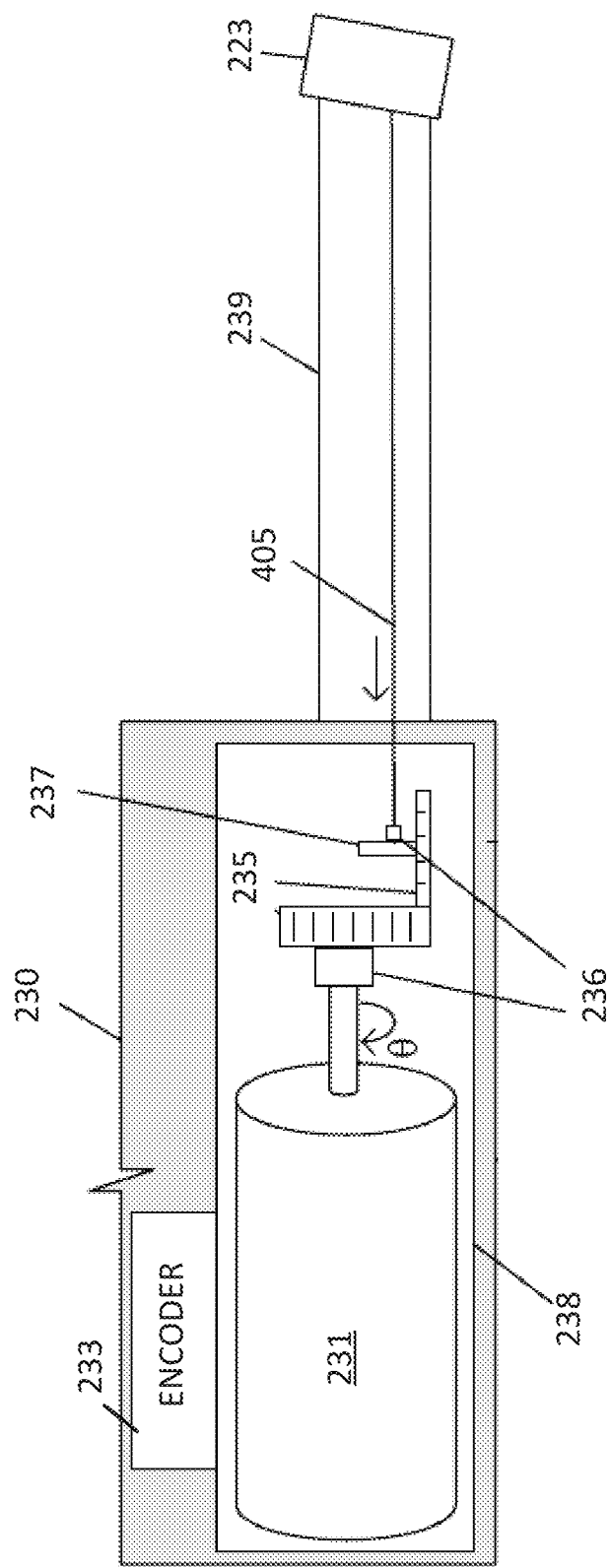

FIG. 8 illustrates a more detailed view of the cable drive system. A motor 231 operates the cables 405. The motor 231 may be connected directly to a shaft for winding the cables 405 in particular sequences in order to move the wrist 223. In the example illustrated in FIG. 8, the motor 231 drives a gear train 235 to rotate a capstan 237 that the cable wraps around. A variety of sensors may be included in the cable drive system. A position encoder 233 may be a rotary position encoder that monitors motor shaft position and encodes the current motor shaft position, e.g., to a value representing angular position. A sensor 236 may include a tension sensor that is coupled to a respective cable or a torque sensor that measures torque of a respective motor coupled to the cable. Measured torque (a rotational force) can be converted to tension (a linear force). Each cable may have an initial tension (a pre-tension) at a starting 'relaxed' position of the tool. In some embodiments, the pre-tension is 10N. In some embodiments, where the tool does not require cable pre-tension, the pre-tension value may be set to 0 other low value.

Figure 9:
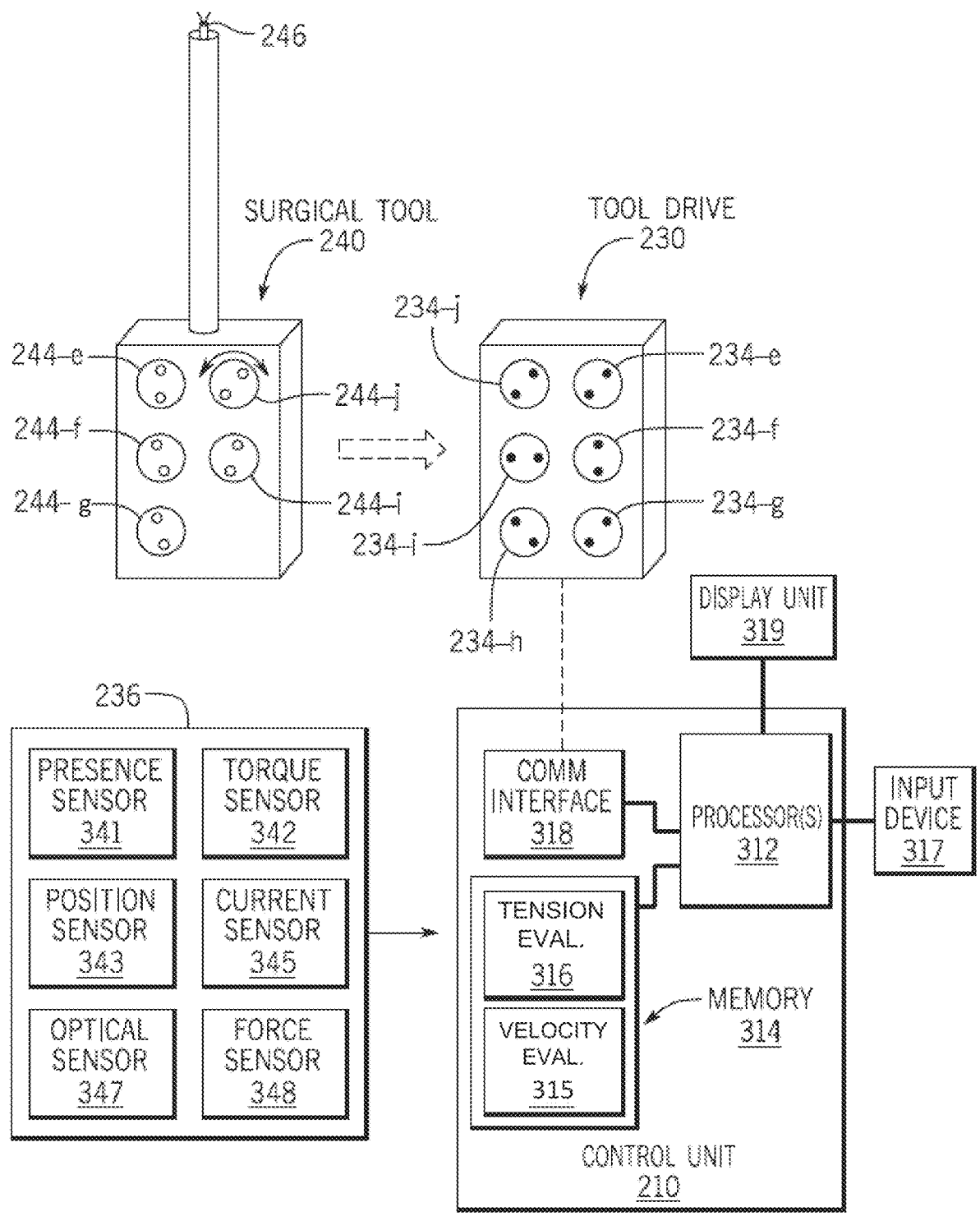

FIG. 9 illustrates an example of the surgical tool 240 that utilizes five tool disks, such as tool disks 244-e, f, g, i, j, arranged in a coplanar fashion on a mating surface of its housing. Each tool disk contributes to at least a portion of the movement and/or activation of end effector 222. Upon detecting the attachment of surgical tool 240 with tool driver 230 (e.g., joining of mating surfaces of the respective housings), control unit 210 (or its processor 312 while executing instructions stored in memory 314) performs a process which determines that only the corresponding five drive disks, such as drive disks 234 e, f, g, i, j, are to be turned (a corresponding actuator 238 is activated) to perform the engagement process.

In some embodiments, the motor operating parameters monitored by the control unit 210 (via sensors 236) are interpreted to mean successful mechanical engagement of a tool disk with a drive disk. The control unit 210 is in communication with and receives sensor data from sensor 236 in an example sensor array including any combination of a presence sensor 341, a torque sensor 342, a position sensor 343, an electrical sensor 345, an optical sensor 347, and a force sensor 348. The sensor array may include separate sensors for different degrees of freedom of the surgical tool (e.g., closure joint, roll joint, or other operation of the surgical tool). That is, the sensor array, or one or more sensors thereof, may be repeated for multiple tool disks 244 in the tool driver 230.

The measurements may include measurements of torque (e.g., a twisting force) applied by the actuator 238-$j$ as measured by the torque sensor 342 or the force sensor 348, measurements of current by the electrical sensor 345 supplied to a motor 231 of the actuator 238-$j$ when attempting to drive the actuator to move at a certain velocity (e.g., where the sensor 236-$j$ may include a current sensing resistor in series with a motor input drive terminal), measurements of electrical impedance by the electrical sensor 345 as seen into the input drive terminals of the motor 231 of the actuator 238 when attempting to drive the motor to move at a certain velocity (e.g., where the sensor 236-$j$ may also include a voltage sensing circuit to measure voltage of the motor input drive terminal), speed of the actuator 238-$j$ (e.g., where the optical sensor 347 may include a position encoder on an output shaft of the actuator 238-$j$ or on a drive shaft of the motor 231), as well as other parameters referred to here as motor operating parameters. The measurements may include presence data from the presence sensor 341, implied from any sensor in the sensor array 236, or determined from the interaction between the information storage unit 242 and the communication interface 232. The position sensor 343 is illustrated separately but may be implemented using a combination of the presence sensor 341, the torque sensor 342, the electrical sensor 345, the optical sensor 347, and the force sensor 348. In one example, additional sensors of the same type may be used for the position sensor 343.

While monitoring the one or more motor operating parameters of a particular actuator, when one or more of these parameters satisfies (e.g., meets or reaches) a predetermined, condition or threshold, the detection of such a situation can be interpreted by control unit 210 as a mechanical engagement event. Note that satisfying the predetermined condition may for example mean that the monitored operating parameter exhibits certain changes, as per the threshold, relative to an operating parameter of another motor that is part of the same actuator 238-$j$ or that is part of another actuator 238-$i$ which is being controlled by the control unit 210 simultaneously during the engagement detection process.

In some embodiments, detection of certain motor operating parameters during operation of the actuator 238-$j$, such as one or more of i) torque that satisfies (e.g., rises and reaches) a torque threshold, ii) motor current that satisfies (e.g., rises and reaches) a current threshold, iii) impedance that drops below an impedance threshold, iv) motor speed dropping below a motor velocity threshold, or a combination thereof, are used by control unit 210 to determine that mechanical engagement of tool disk 244-$j$ to drive disk 234-$j$ has occurred. The following are some examples of such a process.

The control unit 210 including its programmed processor 312 may be integrated into the surgical robotic system 100 (FIG. 1) for example as a shared microprocessor and program memory within the control tower 130. Alternatively, the control unit 210 may be implemented in a remote computer such as in a different room than the operating room, or in a different building than the operating arena shown in FIG. 1. Furthermore, control unit 210 may also include, although not illustrated, user interface hardware (e.g., keyboard, touch-screen, microphones, speakers) that may enable manual control of the robotic arm and its attached surgical tool 240, a power device (e.g., a battery), as well as other components typically associated with electronic devices for controlling surgical robotic systems.

Memory 314 is coupled to one or more processors 312 (generically referred to here as a processor for simplicity) to store instructions for execution by the processor 312. In some embodiments, the memory is non-transitory, and may store one or more program modules, including tension evaluation control 316 and the velocity evaluation control 315, whose instructions configure the processor 312 to perform the calibration and calibration evaluation processes described herein. In other words, the processor 312 may operate under the control of a program, routine, or the execution of instructions stored in the memory 314 as part of tension evaluation control 316 and the velocity evaluation control 315 to execute methods or processes in accordance with the aspects and features described herein.

The memory 314 may include one or more settings, coefficient values, threshold values, tolerance values, calibration values for the surgical tool 240 and/or the tool driver 230. The memory 314 may include specific values for the threshold tension value and/or the velocity threshold described below. These values may be stored in memory 314 as a configuration file, table, or matrix. Some values in the configuration file may be provided by the user, some may be accessed or retrieved based on identifiers of the surgical tool 240 or tool driver 230, and others may be set by the control unit 210.

Figure 10:
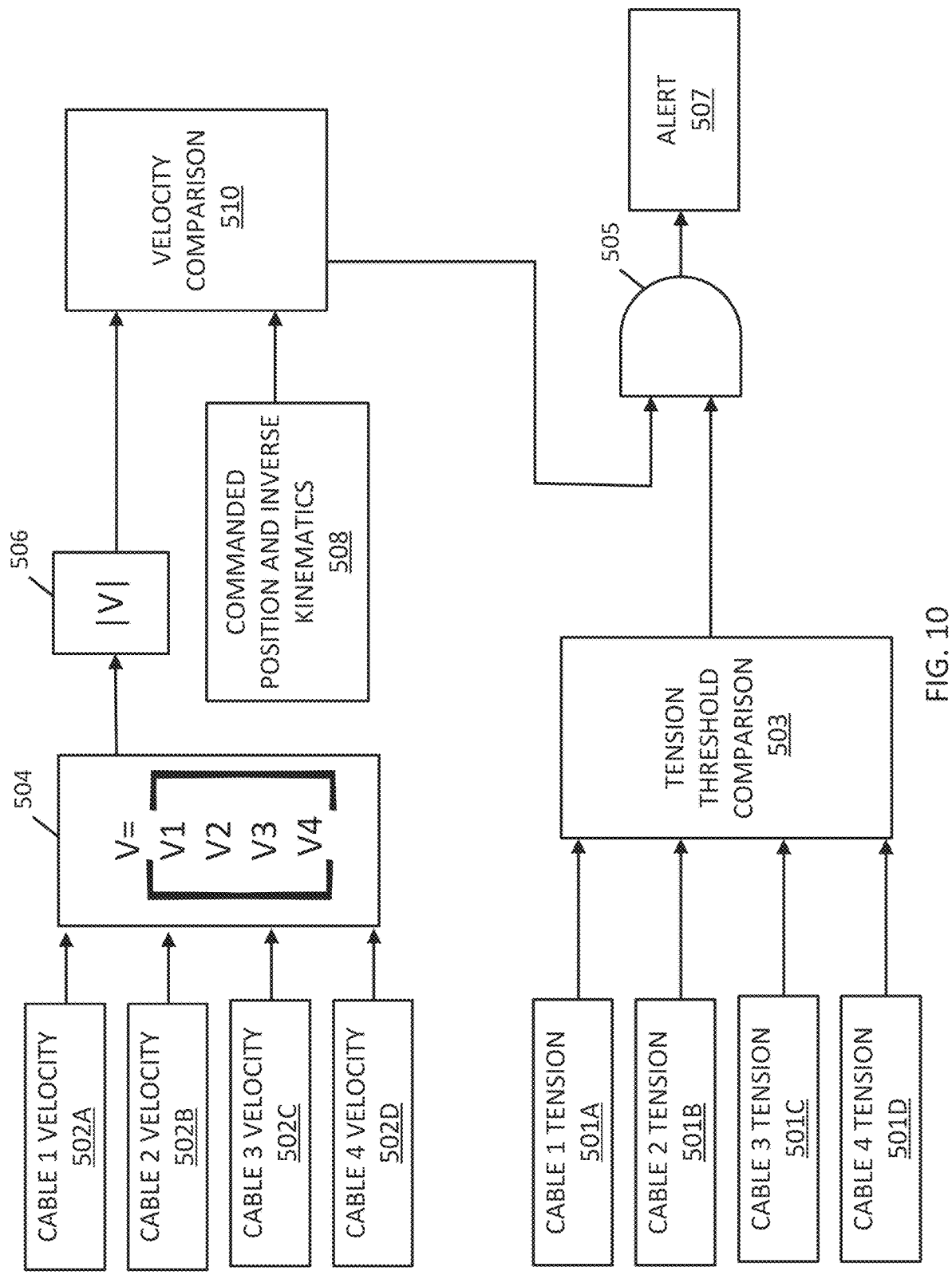

FIG. 10 illustrates a block diagram for a procedure or technique that may be carried out by any of the systems described herein, for example, by a controller, such as the control unit 210. Each act or block may refer to a separate process that may have many steps. The sequence illustrates is only an example and the steps may be performed in any order. Additional, different, or fewer blocks may be included.

As described above, each or one or more of the actuators 238 or motors 231 may be associated with a sensor such as the torque sensor 342. Respective torque sensors 342 measure the torque on actuators 238. The tension in a cable coupled to the actuator 238 is determined based on the measured torque. The torque on the actuator 238 measured by the torque sensor 342 may be multiplied by the radius of the actuator 238 to equal to the tension in the respective coupled cable. The control unit 210 may calculate a set of cable tensions 501A-D including tension values from the torques on the corresponding actuators and/or drive train between the actuator and the cable.

The control unit 210 may calculate the tension of at least one of the cables from an inverse kinematics model for the surgical tool 240. For example, the user input from the input device 317 may request a particular position or direction of motion in joint space. The control unit 210 translates the commanded position from the inverse kinematics model including the B matrix described above to convert the commanded position in actuator space or directly to cable space. The inverse kinematics model includes a relationship between the torque detected at respective ones of the plurality of motors and the tension of the at least one of the plurality of cables according to an inverse kinematics matrix.

Alternatively, the control unit 210 may receive the tension for at least one the cables from a tension sensor that is coupled to a respective cable. In all of these examples, the control unit 210 identifies a tension of at least one of the plurality of cables derived from at least one of the forces detected by the sensors.

The control unit 210 performs tension threshold comparison 503 (e.g., included in the tension evaluation control 316) to compare the tension of the at least one of the cables to a threshold tension value. The output of the threshold comparison 503 may be a binary value that corresponds to a first value (e.g., high value or 1) when the tension is less than the threshold tension value and a second value (e.g., low value or 0) when the tension is greater than the threshold tension value.

The control unit 210 may also determine a set of cable velocities 502A-D based on sensor data for the corresponding actuator 238. In one example, the position encoder 233 provides sensor data for the position of the actuator 238. The change in rotational position of the actuator 238 is translated to the linear velocity of the cables. Alternatively, the set velocity of the cables 502A-D is based on the sensor data for motor torque.

Another example of the calculation of the set of cable velocities 502A-D accounts for the capstan 237 and/or gear train. The set of cable velocities 502A-D may be determined based in on actuator position and a radius of the capstan 237. The capstan radius is the distance that a respective cable fixes to and wraps around when the capstan 237 rotates. Rotation of the capstan can be effected through one or more gears that translate rotational motion of motor 231 to rotational motion of the capstan 237. When the capstan is rotated, cable position and cable tension changes accordingly, depending on an amount and direction of rotation.

In some embodiments, measured cable position (C) is determined through the product of actuator position (x) and a radius (r) as shown by Equation 10. The radius (r) may be the radius of the actuator or the radius of the capstan, which may be adjusted by the gear ratio of the gear train.

$$C = x * r \qquad \text{Eq. 10}$$

The change in cable position (C) is the velocity of the cable (V) as shown by Equation 11. The derivative of cable position with respect to time is cable velocity. Likewise, the derivative of actuator position with respect to time multiplied by the radius is cable velocity.

$$V = dC/dt = dx/dt * r \qquad \text{Eq. 10}$$

The control unit 210 generates velocity vector 504 (e.g., using velocity evaluation control 315) from the set of cable velocities 502A-D. The control unit 210 may identify a velocity value for each of the plurality of cables calculated from any of the techniques described above. The velocity vector 504 includes an entry for each cable in the cable drive system. The velocity vector 504 may be arranged such that antagonistic pairs of cables are in predetermined positions in the velocity vector 504. For example, the velocity values for antagonistic pairs of cables may be adjacent in the velocity vector 504.

The control unit 210 may calculate a measured velocity norm value 506 from the velocity vector 504. The entries of the velocity vector 504 are squared and summed, and the square root of the result is the velocity norm value 506, as shown in Equation 11. The magnitude of the velocity vector 504 is the measured velocity norm value 506. Thus, the measured velocity norm value ($V_{measured}$) is a single value that represents the measured velocities ($MV_1$, $MV_2$, ... $MV_n$) of all of the cables in the cable drive system.

$$V_{measured} = \sqrt{MV_1^2 + MV_2^2 + ... MV_n^2} \qquad \text{Eq. 11}$$

The measured velocity norm value 506 may be compared to commanded velocities. The commanded velocities are the expected velocities of the cable based on the commands sent to the actuator 238. When the commanded velocities are different from the measured velocities, there has been unexpected behavior. The engagement between the actuator and the sterile adapter may have been disengaged or otherwise compromised. When this happens, the energy stored in one or more cables as tension can move the wrist in an unexpected manner.

The control unit 210 may calculate a commanded velocity norm value from the commanded velocity values for the cable based on the user input. The commanded velocity values are squared and summed, and the square root of the result is the commanded velocity norm value ($V_{command}$), as shown in Equation 12. The commanded velocity norm value is a single value that represents the commanded velocities ($CV_1$, $CV_2$, ... $CV_n$) of all of the cables in the cable drive system.

$$V_{command} = \sqrt{CV_1^2 + CV_2^2 + ... CV_n^2} \qquad \text{Eq. 11}$$

The control unit 210 performs the velocity threshold comparison 510 (e.g., using velocity evaluation control 315) to compare the velocity norm value to a statistic velocity threshold. The statistic velocity threshold may be set equal to the commanded velocity norm value so that the comparison is a direct comparison. The output of the threshold comparison 503 may be a binary value that corresponds to a first value (e.g., high value or 1) when the velocity is greater than the statistic velocity threshold and a second value (e.g., low value or 0) when the tension is less than the statistic velocity threshold.

The statistic velocity threshold may be the difference in the measured velocity norm value and the commanded velocity norm value that is statistically significant. For example, the measured velocity norm value and/or the commanded velocity norm value may be monitored by the control unit 210 over time to determine how much of a change in the measured velocity norm value and/or the commanded velocity norm value indicates that one or more of the cables has experienced a release of energy due to a disconnection or breakage and not simply an inconsequential variation in the data.

The statistic velocity threshold may be calculated, in part, from a Bayesian filter. For example, a Bayesian filter may analyze a time series of data from the measured velocity norm value, the commanded velocity norm value, or a difference between the measured velocity norm value and the commanded velocity norm value. The Bayesian filter may determine a joint probability distribution over any of these variables in time to identify statistically significant changes in the variables and filter out variations that are merely noise.

The statistic velocity threshold may be determined from a statistical hypothesis test (e.g., chi-squared test). The statistical hypothesis determines whether there is a statistically significant difference between the measured velocity norm value and the expected value from the commanded velocity norm value.

The statistic velocity threshold is calculated, in part, from an average of the velocity norm value at a first time and the velocity norm value at a second time. For example, the statistic velocity threshold is calculated, in part, from a standard deviation of a time series of data including the velocity norm value at the first time and the velocity norm value at the second time.

An AND gate 505, which may be included merely for graphical representation, represents the logical operation for the output of the tension threshold comparison 503 and the velocity comparison threshold 510. There may be no component corresponding to the gate 505, which may be only a graphical representation. When the output of the velocity threshold comparison 510 indicates that the velocity is greater than the statistic velocity threshold and the tension threshold comparison 503 indicates the measured tension is less than the threshold tension value the output of the AND gate 505 may be high and cause the control unit 210 to generate one or more messages. The control unit 210 is configured to identify a disengagement of at least one of the plurality of cables or associated motors based on the first comparison and the second comparison.

The message may be indicative of a disengagement of a cable or a disengagement of the motor from the sterile adapter, which results in a disengaged cable. The control unit 210 may generate the message in response to the disengagement of at least one of the cables. The message may specify the cable. For example, the cable may be identified by the lowest tension value for the set of cable tensions 501A-D based on the torques on the corresponding actuator 238 or from the inverse kinematics model for the surgical tool 240.

The message may be an alert 507 to the user. For example, the message may state that an error has occurred. The message may provide instructions for the user to handle the error such as reconnecting the disengaged cable or the disengaged motor. The message may instruct the user to remove the tool. The message may instruct the user to replace the tool with a new tool.

The message may be an internal message that instructs the control unit 210 to disable the surgical tool 240. Thus, when a disengagement is detected, the surgical tool 240 is disabled. The control unit 210 may generate an error command that disables the surgical tool 240 in response to the message when the disengagement is detected. Re-enabling the tool may require entering a code to the surgical tool 240 or providing a factor reset command to the surgical tool 240.

The message may be an external message that is communicated to an external device. For example, the message may be sent to a manufacturer or other entity that dispatches services for the surgical tool. The external device or the control unit 210 may track the occurrences of messages or alerts at the surgical tool 240, and when a set number of messaged have occurred, a fatal error may be assigned to the surgical tool 240 and the surgical tool 240 permanently disabled. The message may be logged by the external device, along with other surgical tools, to identify trends in the deployment of a particular model of surgical tool.

Figure 11:
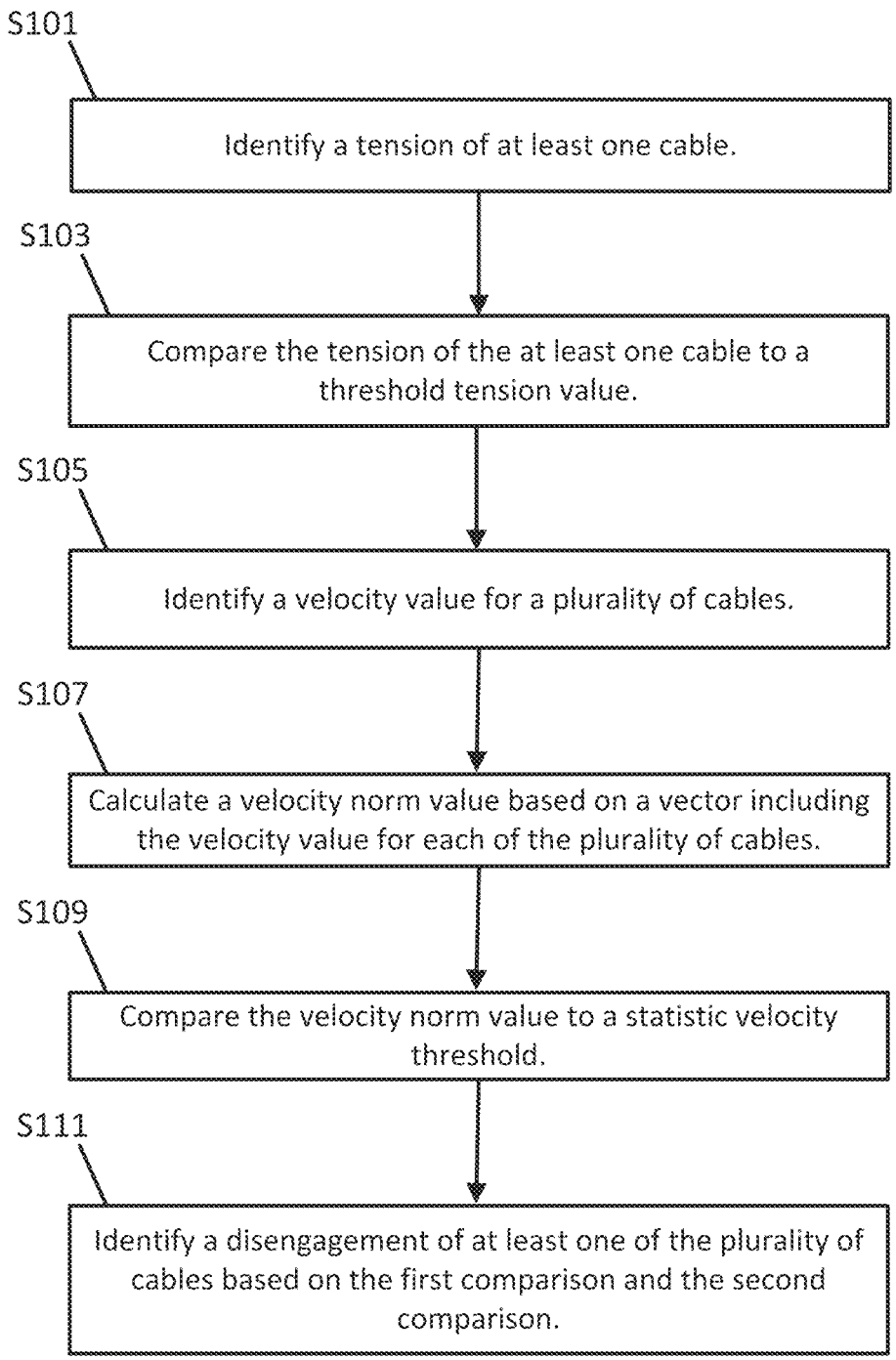

FIG. 11 describes a process for detection of a cable malfunction. The process may be performed by a programmed processor (also referred to here as processor or controller), configured according to instructions stored in memory (e.g., the processor 312 and the memory 314 of FIG. 9, where the processor 312 is configured according to the instructions of the tension evaluation control 316 and the velocity evaluation control 315). Additional, different, or fewer acts than those in FIG. 11 may be performed.

At act S101, the processor 312 identifies a tension in a cable of the surgical tool. The processor 312 may calculate a value for the tension or receive the value from a sensor directly or indirectly. Tension values may be received or calculated repeatedly such as at a predetermined time interval. Tension values may be identified at a sample rate such as every 1 second, 100 milliseconds, or 10 milliseconds. Tension values may be received for any number or all of the cables in the surgical tool.

In one example, the tension is measured or received only at specific times. For example, the processor 312 may determine that the cables are tensioned based on the movement of the end effector. In some examples, the cables, or a subset of the cables, may not be tensioned when a degree of freedom (e.g., roll, pitch, yaw, or jaw) changes direction. The degree of freedom changes direction when the corresponding angle for the degrees of freedom transitions from increasing in value to decreasing in value or from decreasing in value to increasing in value.

At act S103, the processor 312 performs a comparison of the tension of the at least one cable to a threshold tension value extracted from memory 314. The threshold tension value may be set by the user or manufacturer. Alternatively, the threshold tension value may be variable over time. The threshold tension may be based on an average of past tension values such as twice the average of past tension values over a time window. The threshold tension value may be different for different cables. The threshold tension value may be different for pairs of cables. In one example, for each pair of antagonistic cables, the comparison is made only for one of the antagonistic pair at a time. In another example, the threshold tension value is assigned to a pair of antagonistic cables and the comparison is for the sum of the tension values for the pair of antagonistic cables.

At act S105, the processor 312 identifies a velocity for each of the cables of the surgical tool or at least multiple cables of the surgical tool. The processor 312 may calculate a value for the velocities or receive the value from a sensor directly or indirectly. Velocity values may be received or calculated repeatedly such as at a predetermined time interval. Velocity values may be identified at a sample rate such as every 1 second, 100 milliseconds, or 10 milliseconds.

At act S107, the processor 312 calculates a velocity norm or representative value for all of the cables of the surgical tool or for multiple cables of the surgical tool. The velocity norm may be a sum of the velocity values. The velocity norm may include a sum of squares of the velocity values. The velocity sum may be the square root of the sum of the squares of the velocity values. Other examples for the velocity that combine the relative velocities of the cables of the surgical tool are possible.

At act S109, the processor 312 compares the velocity norm to a velocity threshold. The velocity threshold may be set by the user or manufacturer. Alternatively, the velocity threshold may be variable over time. The velocity threshold may be set based on past values such as twice the average of the velocity norm over a time window.

At act S111, the processor 312 detects a malfunction of the surgical tool. The malfunction is based on the comparison for tension and the comparison for velocity. When the tension is below the tension threshold and the velocity is above the threshold, the processor 312 identifies a malfunction with the cable. The malfunction may indicate a disengagement between the sterile adapter and the surgical tool. The malfunction may be disengagement of at least one cable.

The processor 312 may generate a command for remedial action in response to the determination of the malfunction in the surgical tool. The remedial action may disable the surgical tool. The surgical tool may be disabled for a predetermined time, until user intervention (e.g., reset switch) takes place, or until the surgical tool is reconfigured. The reconfiguring of the surgical tool may include homing and/or calibration. The reconfiguring of the surgical tool may include replacing one or more cables.

Herein, the phrase "coupled with" is defined to mean directly connected to or indirectly connected through one or more intermediate components. Such intermediate components may include both hardware- and software-based components. Further, to clarify the use in the pending claims and to hereby provide notice to the public, the phrases "at least one of <A>, <B>, . . . and <N>" or "at least one of <A>, <B>, . . . <N>, or combinations thereof" are defined by the Applicant in the broadest sense, superseding any other implied definitions hereinbefore or hereinafter unless expressly asserted by the Applicant to the contrary, to mean one or more elements selected from the group comprising A, B, . . . and N, that is to say, any combination of one or more of the elements A, B, . . . or N including any one element alone or in combination with one or more of the other elements which may also include, in combination, additional elements not listed.

The disclosed mechanisms may be implemented at any logical and/or physical point(s), or combinations thereof, at which the relevant information/data (e.g., message traffic and responses thereto) may be monitored or flows or is otherwise accessible or measurable, including one or more gateway devices, modems, computers or terminals of one or more market participants, e.g., client computers, etc.

One skilled in the art will appreciate that one or more modules described herein may be implemented using, among other things, a tangible computer-readable medium comprising computer-executable instructions (e.g., executable software code). Alternatively, modules may be implemented as software code, firmware code, specifically configured hardware or processors, and/or a combination of the aforementioned.

The operations of computer devices and systems shown in FIGS. 1-11 may be controlled by computer-executable instructions stored on a non-transitory computer-readable medium. For example, the exemplary computer device or control unit 210 may store computer-executable instructions, generate electronic messages, extracting information from the electronic messages, executing actions relating to the electronic messages, and/or calculating values from the electronic messages to facilitate any of the algorithms or acts described herein. Numerous additional servers, computers, handheld devices, personal digital assistants, telephones and other devices may also be connected to control unit 210.

Figure 3A:
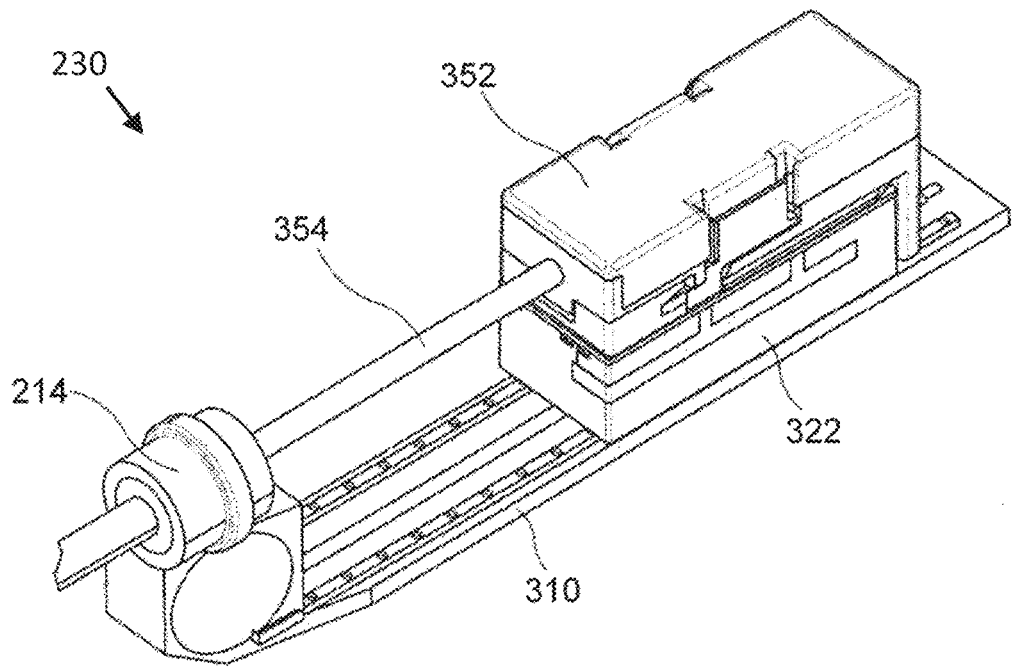
Figure 3B:
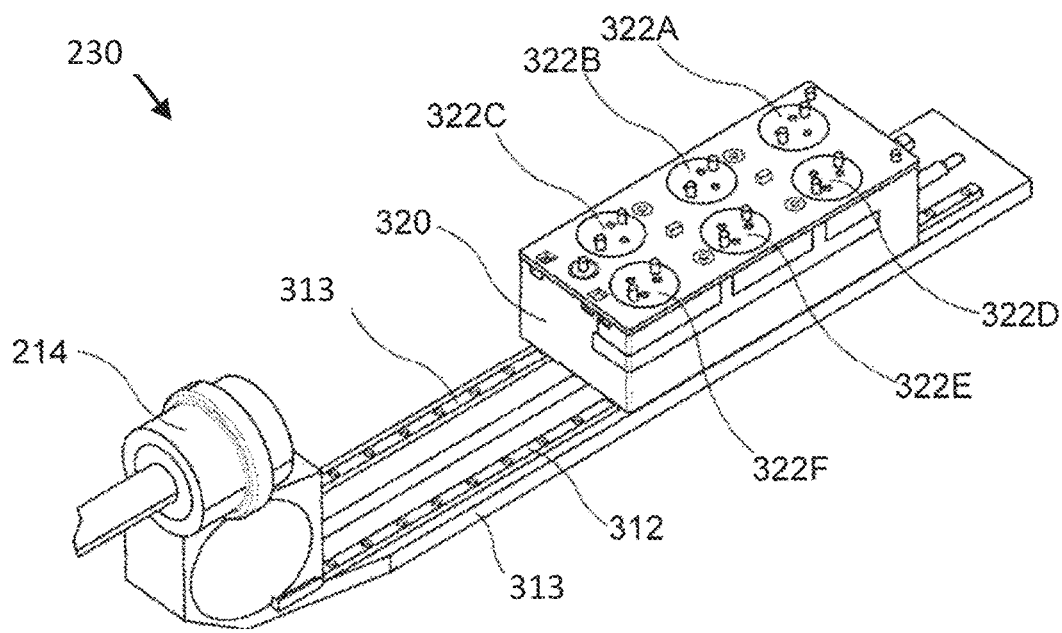

As illustrated in FIG. 3, the computer system may include a processor 312 implemented by a central processing unit (CPU), a graphics processing unit (GPU), or both. The processor 312 may be a component in a variety of systems. For example, the processor 312 may be part of a standard personal computer or a workstation. The processor 312 may be one or more general processors, digital signal processors, specifically configured processors, application specific integrated circuits, field programmable gate arrays, servers, networks, digital circuits, analog circuits, combinations thereof, or other now known or later developed devices for analyzing and processing data. The processor 312 may implement a software program, such as code generated manually (i.e., programmed).

The computer system includes memory 314 that can communicate via a bus. The memory 314 may be a main memory, a static memory, or a dynamic memory. The memory 314 may include, but is not limited to, computer-readable storage media such as various types of volatile and non-volatile storage media, including but not limited to random-access memory, read-only memory, programmable read-only memory, electrically programmable read-only memory, electrically erasable read-only memory, flash memory, magnetic tape or disk, optical media and the like. In one embodiment, the memory 314 includes a cache or random-access memory for the processor 312. In alternative embodiments, the memory 314 is separate from the processor 312, such as a cache memory of a processor, the system memory, or other memory. The memory 314 may be an external storage device or database for storing data. Examples include a hard drive, compact disk ("CD"), digital video disc ("DVD"), memory card, memory stick, floppy disk, universal serial bus ("USB") memory device, or any other device operative to store data. The memory 314 is operable to store instructions executable by the processor 312. The functions, acts or tasks illustrated in the figures or described herein may be performed by the programmed processor 312 executing the instructions stored in the memory 314. The functions, acts or tasks are independent of the particular type of instructions set, storage media, processor or processing strategy and may be performed by software, hardware, integrated circuits, firmware, microcode and the like, operating alone or in combination. Likewise, processing strategies may include multiprocessing, multitasking, parallel processing and the like.

The computer system may further include a display unit 319, such as a liquid crystal display (LCD), an organic light emitting diode (OLED), a flat panel display, a solid-state display, a cathode ray tube (CRT), a projector, a printer or other now known or later developed display device for outputting determined information. The display 319 may act as an interface for the user to see the functioning of the processor 312, or specifically as an interface with the instructions stored in the memory 314 or elsewhere in the control unit 210.

Additionally, the computer system may include an input device 317 configured to allow a user to interact with any of the components of system. The input device 317 may be a number pad, a keyboard, or a cursor control device, such as a mouse, or a joystick, touch screen display, remote control or any other device operative to interact with the control unit 210.

The present disclosure contemplates a computer-readable medium that includes instructions or receives and executes instructions responsive to a signal, so that a device connected to a network can communicate voice, video, audio, images or any other data over the network. Further, the instructions may be transmitted or received over the network via a communication interface 318. The communication interface 318 may be a part of the processor 312 or may be a separate component. The communication interface 218 may be a physical connection in hardware. The communication interface 318 is configured to connect with a network, external media, the display unit 319, or any other components in the system, or combinations thereof. The connection with the network may be a physical connection, such as a wired Ethernet connection or may be established wirelessly. Likewise, the additional connections with other components of the system may be physical connections or may be established wirelessly.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings and described herein in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the described embodiments should not be understood as requiring such separation in all embodiments, and it should be understood that the described program components and systems can generally be integrated together in a single software product or packaged into multiple software products.

What is claimed is:

1. An apparatus for detecting disengagement of a surgical tool, the apparatus comprising:
   an end effector connected to and driven by a plurality of cables of a tool driver;
   a plurality of sensors configured to detect forces associated with the plurality of cables; and
   one or more processors configured to:
      identify a tension of at least one of the plurality of cables derived from at least one of the forces detected by the plurality of sensors;
      perform a first comparison of the tension of the at least one of the plurality of cables to a threshold tension value;
      identify a velocity value for each of the plurality of cables;
      calculate a velocity norm value based on a vector including the velocity value for each of the plurality of cables;
      perform a second comparison of the velocity norm value to a statistic velocity threshold; and
      identify a disengagement of at least one of the plurality of cables or associated components based on the first comparison and the second comparison.

2. The apparatus of claim 1, wherein the velocity norm value is a magnitude of the vector including the velocity value for each of the plurality of cables.

3. The apparatus of claim 2, one or more processors configured to:
   calculate the statistic velocity threshold, in part, from a commanded velocity.

4. The apparatus of claim 3, wherein the statistic velocity threshold is calculated, in part, from a Bayesian filter.

5. The apparatus of claim 3, wherein the statistic velocity threshold is calculated, in part, from an average of the velocity norm value at a first time and the velocity norm value at a second time.

6. The apparatus of claim 5, wherein the statistic velocity threshold is calculated, in part, from a standard deviation of a time series of data including the velocity norm value at the first time and the velocity norm value at the second time.

7. The apparatus of claim 6, one or more processors configured to:
   calculate a chi squared value for the time series of data.

8. The apparatus of claim 1, further comprising:
   a plurality of motors coupled to the plurality of cables, respectively, wherein the plurality of sensors detect torque at respective ones of the plurality of motors.

9. The apparatus of claim 8, one or more processors configured to:
   calculate the tension of at least one of the plurality of cables from an inverse kinematics model for the surgical tool.

10. The apparatus of claim 9, wherein the inverse kinematics model includes a relationship between the torque detected at respective ones of the plurality of motors and the tension of the at least one of the plurality of cables according to an inverse kinematics matrix.

11. The apparatus of claim 1, one or more processors configured to:
    calculate the velocity value for each of the plurality of cables from an inverse kinematics model.

12. The apparatus of claim 1, one or more processors configured to:
    generate a message in response to the disengagement of at least one of the plurality of cables or associated components.

13. The apparatus of claim 12, wherein the message is a user alert with instructions for a user of the surgical tool.

14. The apparatus of claim 12, wherein the message dispatches services for the surgical tool.

15. The apparatus of claim 12 wherein the message is an error command that disables the surgical tool.

16. A method for detecting disengagement of a surgical tool connected to and driven by a plurality of cables, the method comprising:
    identifying a tension of at least one of the plurality of cables derived from at least one force detected by a plurality of sensors;
    performing a first comparison of the tension of the at least one of the plurality of cables to a threshold tension value;
    identifying a velocity value for each of the plurality of cables;
    calculating a velocity norm value based on a vector including the velocity value for each of the plurality of cables;
    performing a second comparison of the velocity norm value to a statistic velocity threshold; and
    identifying a disengagement based on the first comparison and the second comparison.

17. The method of claim 16, wherein the velocity norm value is a magnitude of the vector including the velocity value for each of the plurality of cables.

18. The method of claim 16, wherein the statistic velocity threshold is based, at least in part, on a commanded velocity.

19. The method of claim 16, wherein the statistic velocity threshold is based, at least in part, on the velocity norm value at a first time and the velocity norm value at a second time.

20. An apparatus comprising:
- a memory configured to store a threshold tension value and a statistic velocity threshold; and
- a controller configured to perform a first comparison of a tension of at least one of a plurality of cables connected to an end effector of a surgical tool to the threshold tension value and perform a second comparison of a velocity norm value to the statistic velocity threshold, wherein a disengagement of at least one cable of the plurality of cables is determined based on the first comparison and the second comparison, wherein the velocity norm value is based on a vector for the plurality of cables.

* * * * *